US009253989B2

(12) United States Patent
Smith et al.

(10) Patent No.: US 9,253,989 B2
(45) Date of Patent: *Feb. 9, 2016

(54) COMBINED USED OF LIPO-CHITOOLIGOSACCHARIDES AND CHITINOUS COMPOUNDS FOR ENHANCED PLANT GROWTH AND YIELD

(71) Applicant: Novozymes BioAg A/S, Bagsvaerd (DK)

(72) Inventors: Raymond Stewart Smith, Pewaukee, WI (US); Robert Martin Osburn, Mequon, WI (US)

(73) Assignee: Novozymes BioAg A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/714,556

(22) Filed: Dec. 14, 2012

(65) Prior Publication Data

US 2013/0109567 A1    May 2, 2013

Related U.S. Application Data

(63) Continuation of application No. 12/521,375, filed as application No. PCT/US2008/000235 on Jan. 8, 2008, now Pat. No. 8,357,631.

(60) Provisional application No. 60/879,436, filed on Jan. 9, 2007, provisional application No. 60/980,287, filed on Oct. 16, 2007.

(51) Int. Cl.
*A01N 63/02* (2006.01)
*A01N 43/16* (2006.01)

(52) U.S. Cl.
CPC ............... *A01N 63/02* (2013.01); *A01N 43/16* (2013.01)

(58) Field of Classification Search
None
See application file for complete search history.

(56) References Cited

U.S. PATENT DOCUMENTS

| | | | |
|---|---|---|---|
| 4,536,207 A | 8/1985 | McCandliss et al. | |
| 5,175,149 A | 12/1992 | Stacey et al. | |
| 5,321,011 A | 6/1994 | Stacey et al. | |
| 5,549,718 A | 8/1996 | Lerouge et al. | |
| 5,646,018 A | 7/1997 | Broughton et al. | |
| 5,702,752 A | 12/1997 | Gugger et al. | |
| 5,733,851 A | 3/1998 | Villanueva et al. | |
| 5,922,316 A | 7/1999 | Smith et al. | |
| 5,990,291 A | 11/1999 | Waggle et al. | |
| 6,146,668 A | 11/2000 | Kelly et al. | |
| 6,193,988 B1 | 2/2001 | Stoner, II et al. | |
| 6,200,929 B1 * | 3/2001 | Horibe et al. | 504/127 |
| 6,979,664 B1 | 12/2005 | Smith et al. | |
| 7,250,068 B1 | 7/2007 | Smith et al. | |
| 2011/0281729 A1 | 11/2011 | Beau et al. | |

FOREIGN PATENT DOCUMENTS

| | | |
|---|---|---|
| WO | 0059949 | 10/2000 |
| WO | WO 03/077654 | 9/2003 |
| WO | WO 2004/093542 | 11/2004 |
| WO | WO 2005/063784 | 7/2005 |

OTHER PUBLICATIONS

Manjula, K. et al. Chitin-supplemented formulations improve biocontrol and plant growth promoting efficiency of Bacillus subtilis AF1. Canadian Journal of Microbiology, 2001, 47(7) 618-625 (abstract only).*
California Department of Pesticide Regulation, Pesticide Info Sheet. revised 2009, http://web.archive.org/web/20090828131314/http://www.cdpr.ca.gov/docs/dept/factshts/residu2.pdf.*
International Search Report, dated Jun. 11, 2008.
Prithiviraj et al., "A host-specific bacteria-to-plant signal molecule (Nod factor) enhances germination and early growth of diverse crop plants," *Planta*, vol. 16, No. 3, Jan. 2003, pp. 437-445.
Ferguson et al., "Signaling Interactions During Nodule Development," *Journal of Plant Growth Regulation*, vol. 22, No. 1, Sep. 2003, pp. 47-72.
Oláh et al., "Nod factors and a diffusible factor from arbuscular mycorrhizal fungi stimulate lateral root formation in *Medicago truncatula* via the DMI1/DMI2 signalling pathway," *The Plant Journal*, vol. 44, Issue 2, Oct. 2005, pp. 195-207.
Díaz et al, "Heterologous Rhizobial Lipochitin Oligosaccharides and Chitin Oligomers Induce Cortical Cell Divisions in Red Clover Roots, Transformed with the Pea Lectin Gene," *Molecular Plant-Microbe Interactions*, vol. 13, No. 3, Mar. 2000, pp. 268-276.
Collinge et al., "Plant chitinases," *The Plant Journal*, vol. 3, Issue 1, Jan. 1993, pp. 31-40.
Jain et al., "Plant flavonoids: Signals to legume nodulation and soil microorganisms," *Journal of Plant Biochemistry and Biotechnology*, vol. 11, No. 1, 2002, pp. 1-10.
Shaw et al., "Perception and modification of plant flavonoid signals by rhizosphere microorganisms," *Environmental Microbiology*, vol. 8, Issue 11, Nov. 2006, pp. 1867-1880.
Spaink et al., "Root Nodulation and Infection Factors Produced by Rhizobial Bacteria," *Annual Review of Microbiology*, vol. 54, Oct. 2000, pp. 257-288.
D'Haeze et al., "Nod factor structures, responses, and perception during initiation of nodule development," *Glycobiology*, vol. 12, No. 6, Jun. 2002, pp. 79R-105R.
Samain et al., "Gram-scale synthesis of recombinant chitooligosaccharides in *Escherichia coli*," *Carbohydrate Research*, vol. 302, Issues 1-2, Jul. 11, 1998, pp. 1-122 (Jul. 11, 1997).
Hungria and Stacey, "Molecular signals exchanged between host plants and rhizobia: Basic aspects and potential application in agriculture," *Soil Biology & Biochemistry*, vol. 29, Issues 5-6, May-Jun. 1997, pp. 819-830.

(Continued)

*Primary Examiner* — Mina Haghighatian
*Assistant Examiner* — Erin Hirt
(74) *Attorney, Agent, or Firm* — Adam Rucker

(57) ABSTRACT

Compositions and methods for enhancing plant growth and crop yield in legumes and non-legumes are described. The compositions include lipo-chitooligosaccharides in combination with chitins/chitosans or in combination with flavonoid compounds or in combination with a herbicide. The method includes applying the compositions to seeds and/or plants either concomitantly or sequentially.

20 Claims, No Drawings

(56) References Cited

OTHER PUBLICATIONS

Pochanavanich et al, "Fungal chitosan production and its characterization," *Letters in Applied Microbiology*, vol. 35, Issue 1, Jul. 2002, pp. 17-21.

Ralston et al., "Partial Reconstruction of Flavonoid and Isoflavonoid Biosynthesis in Yeast Using Soybean Type I and Type Ii Chalcone Isomerases," *Plant Physiology*., vol. 137, Issue 4, Apr. 2005, pp. 1375-1388.

Pedersen, "Soybean Growth and Development," Iowa State University Extension Bulletin PM 1945, May 2004.

Staehelin et al., "Perception of *Rhizobium* nodulation factors by tomato cells and inactivation by root chitinases," *Proc. Natl. Acad. Sci. USA*, vol. 91, Mar. 1994, pp. 2196-2200.

Leibovitch, S.; Migner, P.; Zhang, F.; Smith, D.L.J. Agronomy & Crop Science, 2001, 187, 281-292.

Complaint filed on Jun. 20, 2013 in *Loken-Flack, LLC* v. *Novozymes Bioag, Inc.*, No. 1:13-cv-01617 (D. Colo. filed Jun. 20, 2013) (total 5 pages).

Defendant's Answer filed on Oct. 28, 2013 in *Loken-Flack, LLC* v. *Novozymes Bioag, Inc.*, No. 1:13-cv-01617 (D. Colo. filed Jun. 20, 2013) (total 7 pages).

Letter dated Oct. 16, 2013 from John J. Cotter to Craig R. Miles (without enclosure) (total 1 page).

Affidavit of Robert M. Osburn Revoking the Miles 2012 Declaration and the Blakley 2012 Power of Attorney, including Exhibits a through I (total 98 pages).

Letter dated Nov. 1, 2013 from Craig R. Miles to John J. Cotter (total 2 pages).

Letter dated Oct. 29, 2013 from John J. Cotter to Craig R. Miles (total 1 page).

Search Report for Chinese Application No. 201310365298.1 dated Dec. 4, 2014 (with English translation).

Second Office Action mailed Dec. 12, 2014 in Chinese Application No. 201310365298.1 (with English translation).

Canadian Office Action mailed Jan. 23, 2015, in Canadian Application No. 2,674,602.

Indonesian Office Action mailed Jan. 28, 2015 in Indonesian Application No. W00 2009 01907.

* cited by examiner

COMBINED USED OF LIPO-CHITOOLIGOSACCHARIDES AND CHITINOUS COMPOUNDS FOR ENHANCED PLANT GROWTH AND YIELD

CROSS REFERENCE TO RELATED APPLICATIONS

This application is a continuation application of U.S. patent application Ser. No. 12/521,375, filed Jun. 26, 2009, allowed, which is a U.S. National Phase Application under 35 U.S.C. §371 of International Patent Application No. PCT/US08/000235, filed Jan. 8, 2008, which claims priority to U.S. Provisional Patent Application Nos. 60/879,436, filed Jan. 9, 2007 and 60/980,287, filed Oct. 16, 2007, the contents of all of which are incorporated by reference in their entireties for all purposes.

BACKGROUND OF THE INVENTION

Nitrogen fixation plays a vital role in agricultural production by making atmospheric nitrogen available in a form that can be used by plants. In plants of the Leguminoseae family, the symbiotic interaction between the plants and nitrogen-fixing bacteria of the Rhizobiaceae family ("rhizobia") enhances plant growth and crop yield. The symbiotic interaction is initiated when a plant releases flavonoid compounds that stimulate rhizobial bacteria in the soil to produce "Nod-factors." Nod-factors are signaling compounds that induce the early stages of nodulation in plant roots, which lead to the formation of root nodules containing the nitrogen-fixing rhizobial bacteria. Although this process occurs naturally over time in legumes, agricultural procedures have been developed to begin the process earlier. These procedures include providing nitrogen-fixing bacteria to seeds or soil and applying Nod factors directly to seeds or soil prior to or at planting.

Nod factors have recently been shown to also enhance the germination, growth and yield of legumes and non-legumes through processes other than nodulation (U.S. Pat. No. 6,979,664; Prithivaraj et al., *Planta* 216: 437-445, 2003). Although the effects of Nod factors on nodulation have been widely studied and reviewed, e.g., Ferguson and Mathesius, *J. Plant Growth Regulation* 22: 47-72, 2003, the mechanisms for Nod factor effects independent of nodulation are not well understood. Application of Nod factors to seeds of legumes and non-legumes stimulates germination, seedling emergence, plant growth and yield in crop and horticultural plant species, e.g., as described in U.S. Pat. No. 6,979,664 and U.S. Pat. No. 5,922,316. Nod factors have also been shown to enhance root development (Olah, et al., *The Plant Journal* 44:195-207, 2005). Foliar application of Nod factors has also been demonstrated to increase photosynthesis (U.S. Pat. No. 7,250,068), and fruiting and flowering (WO 04/093,542) in crop and horticultural plant species.

Nod factors are lipo-chitooligosaccharide compounds (LCD's). They consist of an oligomeric backbone of β-1,4-linked N-acetyl-D-glucosamine ("GlcNAc") residues with an N-linked fatty acyl chain at the nonreducing end. LCO's differ in the number of GlcNAc residues in the backbone, in the length and degree of saturation of the fatty acyl chain, and in the substitutions of reducing and nonreducing sugar residues. LCO structure is characteristic for each rhizobial species, and each strain may produce multiple LCO's with different structures. LCD's are the primary determinants of host specificity in legume symbiosis (Diaz, Spaink, and Kijne, *Mol. Plant-Microbe Interactions* 13: 268-276, 2000).

LCO synthesis can be stimulated by adding the appropriate flavonoid, for a given genus and species of *rhizobium* during growth of the bacteria. The flavonoid molecules bind to the *rhizobium* and turn on bacterial genes for the production of specific LCD's which are released into the fermentation medium. In nature, leguminous plants release the appropriate flavonoid, which binds to soil rhizobia, turning on genes for LCO production. These LCO's are released by bacteria into the soil, bind to the roots of leguminous plants, and initiate a cascade of plant gene expression that stimulates formation of nitrogen-fixing nodule structures on legume roots. Alternatively, modified and synthetic LCO molecules can be produced through genetic engineering or chemical synthesis. Synthetic LCD's of the same molecular structure interact with plants and stimulate nodulation in the same manner as naturally produced molecules.

Chitins and chitosans, which are major components of the cell walls of fungi and the exoskeletons of insects and crustaceans, are also composed of GlcNAc residues. These compositions have been applied to seeds, roots, or foliage of a broad spectrum of crop and horticultural plants. Chitin and chitosan compositions enhance protection against plant pathogens, in part, by stimulating plants to produce chitinases, enzymes that degrade chitin (Collinge, et al., *The Plant Journal* 3: 31-40, 1993).

Flavonoids are phenolic compounds having the general structure of two aromatic rings connected by a three carbon bridge. Flavonoids are produced by plants and have many functions, e.g., as beneficial signaling molecules, and as protection against insects, animals, fungi and bacteria. Classes of flavonoids include chalcones, anthocyanidins, coumarins, flavones, flavanols, flavonols, flavanones, and isoflavones. (Jain and Nainawatee, *J. Plant Biochem. & Biotechnol.* 11: 1-10, 2002; Shaw, et al., *Environmental Microbiol.* 11: 1867-1880, 2006.)

SUMMARY OF THE INVENTION

The invention includes methods and compositions for increasing plant growth and crop yield. An exemplary composition comprises at least one lipo-chitooligosaccharide and at least one chitinous compound. Another exemplary composition comprises at least one lipo-chitooligosaccharide and at least one flavonoid compound selected from the group consisting of flavones, flavanols, flavonols, flavanones, and isoflavones. A further exemplary composition comprises at least one lipo-chitooligosaccharide and at least one herbicide. An exemplary method comprises administering a composition according to the invention to a plant or seed in an effective amount for enhancing plant growth or crop yield. In another embodiment, the method comprises sequentially treating a plant or a seed with at least one lipo-chitooligosaccharide and at least one chitinous compound or at least one flavonoid compound selected from the group consisting of flavones, flavanols, flavonols, flavanones, and isoflavones.

DETAILED DESCRIPTION OF THE INVENTION

The invention provides compositions and methods for enhancing plant growth and crop yield, and arises from the results of experiments, reported herein, that reveal improved effects of lipo-chitooligosaccharide in combination with chitin/chitosan, flavonoid compounds, or herbicidal compounds on plant growth and crop yield when applied to seeds and/or foliage.

For the purposes of this invention, a "lipo-chitooligosaccharide" ("LCO") is a compound having the general LCO structure, i.e., an oligomeric backbone of β-1,4-linked N-acetyl-D-glucosamine residues with an N-linked fatty acyl chain at the nonreducing end, as described in U.S. Pat. No. 5,549,718; U.S. Pat. No. 5,646,018; U.S. Pat. No. 5,175,149; and U.S. Pat. No. 5,321,011. This basic structure may contain modifications or substitutions found in naturally occurring LCO's, such as those described in Spaink, *Critical Reviews in Plant Sciences* 54: 257-288, 2000; D'Haeze and Holsters, *Glycobiology* 12: 79R-105R, 2002. Also encompassed by the invention are synthetic LCO compounds, such as those described in WO2005/063784, and LCO's produced through genetic engineering. Precursor oligosaccharide molecules for the construction of LCOs may also be synthesized by genetically engineered organisms, e.g., as in Samain et al., *Carbohydrate Research* 302: 35-42, 1997.

LCO's used in embodiments of the invention may be recovered from Rhizobiaceae bacterial strains that produce LCO's, such as strains of *Azorhizobium, Bradyrhizobium* (including *B. japonicum*), *Mesorhizobium, Rhizobium* (including *R. leguminosarum*), *Sinorhizobium* (including *S. meliloti*), and bacterial strains genetically engineered to produce LCO's. These methods are known in the art and have been described, for example, in U.S. Pat. Nos. 5,549,718 and 5,646,018, which are incorporated herein by reference. Commercial products containing LCO's are available, such as OPTIMIZE® (EMD Crop BioScience).

LCO's may be utilized in various forms of purity and may be used alone or with rhizobia. Methods to provide only LCO's include simply removing the rhizobial cells from a mixture of LCOs and rhizobia, or continuing to isolate and purify the LCO molecules thru LCO solvent phase separation followed by HPLC chromatography as described by Lerouge, et. al (U.S. Pat. No. 5,549,718). Purification can be enhanced by repeated HPLC, and the purifed LCO molecules can be freeze-dried for long-term storage. This method is acceptable for the production of LCO's from all genera and species of the Rhizobiaceae.

Within the legume family, specific genera and species of *rhizobium* develop a symbiotic nitrogen-fixing relationship with a specific legume host. These plant host: rhizobia combinations are described in Hungria and Stacey, *Soil Biol. Biochem.* 29: 819-830, 1997, which also lists the effective flavonoid Nod gene inducers of the rhizobial species, and the specific LCO structures that are produced by the different rhizobial species. However, LCO specificity is only required to establish nodulation in legumes. It is not necessary to match LCO's and plant species to stimulate plant growth and/or crop yield when treating seeds or foliage of a legume or non-legume with LCO's.

Chitinous compounds include chitin, (IUPAC: N-[5-[[3-acetylamino-4,5-dihydroxy-6-(hydroxymethyl)oxan-2-yl]methoxymethyl]-2-[[5-acetylamino-4,6-dihydroxy-2-(hydroxymethyl)oxan-3-yl]methoxymethyl]-4-hydroxy-6-(hydroxymethyl)oxan-3-ys]ethanamide), and chitosan, (IUPAC: 5-amino-6-[5-amino-6-[5-amino-4,6-dihydroxy-2-(hydroxymethyl)oxan-3-yl]oxy-4-hydroxy-2-(hydroxymethyl)oxan-3-yl]oxy-2(hydroxymethyl)oxane-3,4-diol). These compounds may be obtained commercially, e.g., from Sigma-Aldrich, or prepared from insects, crustacean shells, or fungal cell walls. Methods for the preparation of chitin and chitosan are known in the art, and have been described, for example, in U.S. Pat. No. 4,536,207 (preparation from crustacean shells), Pochanavanich and Suntornsuk, *Lett. Appl. Microbiol.* 35: 17-21, 2002 (preparation from fungal cell walls), and U.S. Pat. No. 5,965,545 (preparation from crab shells and hydrolysis of commercial chitosan). Deacetylated chitins and chitosans may be obtained that range from less than 35% to greater than 90% deacetylation, and cover a broad spectrum of molecular weights, e.g., low molecular weight chitosan oligomers of less than 15 kD and chitin oligomers of 0.5 to 2 kD; "practical grade" chitosan with a molecular weight of about 150 kD; and high molecular weight chitosan of up to 700 kD. Chitin and chitosan compositions formulated for plant and soil treatment are also commercially available. Commercial products include, for example, ELEXA®-4PDB (Plant Defense Boosters, Inc.) and BEYOND™ (Agrihouse, Inc.).

LCO's and chitins/chitosans are structurally related. Chitin and chitosan can stimulate the production of chitinases by plants, and it has been shown that plant chitinases may inactivate and degrade LCO's as well as chitinous compounds (Staehelin, et al., *P.N.A.S. USA* 91: 2196-2200, 1994; Ferguson and Mathesius, *J. Plant Growth Regulation* 22: 47-72, 2003)). In addition, commercially available chitosan formulations often contain heavy metals that are toxic to rhizobial bacteria and so prevent the production of LCOs. For these reasons, the use of rhizobial bacteria in combination with chitins/chitosans was previously contraindicated. However, as shown in the examples below, it is now demonstrated that application of an LCO compound and chitin/chitosan, either sequentially or simultaneously, to a plant or seed induces beneficial responses in plant growth and yield. While the mechanism for this effect is not proven, one hypothesis is that the LCO compounds bind to specific receptors on the plant or seed and initiate these beneficial responses before LCO degradation by chitinases can occur. Furthermore, this novel treatment method obviates the effects of heavy metals on LCO production by rhizobial bacteria.

In one embodiment of the invention, the composition may be prepared by mixing chitosan, and one or more LCO in an agriculturally appropriate solvent. In a second embodiment, the composition may also contain chitin. Chitosan concentration may range from 0.1 to 15% w/v, preferably from 3 to 12%. Chitin may be included at from 0 to 4% w/v. The LCO concentration may range from $10^{-5}$M to $10^{-14}$M, preferably from $10^{-6}$M to $10^{-10}$M. The LCO component may consist of purified or partly purified LCO, or a mixture of the LCO and the rhizobia that produced the LCO. The agriculturally appropriate solvent is preferably an aqueous solvent, such as water.

Appropriate flavonoids include compounds from the classes of flavones, flavanols, flavonols, flavanones, and isoflavones. Such compounds may include, but are not limited to, genistein, daidzein, formononetin, naringenin, hesperetin, luteolin, and apigenin. Flavonoid compounds are commercially available, e.g., from Natland International Corp., Research Triangle Park, N.C.; MP Biomedicals, Irvine, Calif.; LC Laboratories, Woburn Mass. Flavonoid compounds may be isolated from plants or seeds, e.g., as described in U.S. Pat. No. 5,702,752; U.S. Pat. No. 5,990,291; U.S. Pat. No. 6,146,668. Flavonoid compounds may also be produced by genetically engineered organisms, such as yeast, as described in Ralston, et al., *Plant Physiology* 137: 1375-1388, 2005.

In one embodiment of the invention, the composition may be prepared by combining one or more flavonoid and one or more LCO in an agriculturally appropriate solvent. An "effective amount" of the composition is an amount that increases plant growth or crop yield when compared with the growth or crop yield of plants or seeds that have not been treated with the composition. For example, flavonoid concentration in the composition may range from 20-800 μm, preferably 100-500 μm. LCO concentration in the composition may range from $10^{-5}$ M to $10^{-14}$ M, preferably from $10^{-6}$ M to $10^{-10}$ M. The LCO component may consist of purified or partly purified LCO, or a mixture of the LCO and the rhizobia that produce the LCO. The agriculturally appropriate solvent is preferably an aqueous solvent, such as water.

Although it is efficient and convenient to combine and apply the flavonoid or chitin/chitosan and LCO components in a single mixture, in one embodiment of the invention the flavonoid or chitin/chitosan component and the LCO component may be applied separately and sequentially in either order. Other additives that may be applied either simultaneously or sequentially include fertilizers (e.g., calcium, nitrogen, potassium, phosphorous), micronutrients (e.g., copper, aluminum, magnesium, manganese, and zinc ions), and pesticides (e.g., fungicides, insecticides, herbicides, and nematicides).

In one embodiment of the invention, a composition comprising at least one LCO and at least one herbicide is applied to the foliage of a plant to improve plant growth or crop yield. Suitable herbicides include, but are not limited to bentazon, acifluorfen, chlorimuron, lactofen, clomazone, fluazifop, glufosinate, glyphosate, sethoxydim, imazethapyr, imazamox, fomesafe, flumiclorac, imazaquin, and clethodim. Commercial products containing each of these compounds are readily available. Herbicide concentration in the composition will generally correspond to the labeled use rate for a particular herbicide. LCO concentration in the composition may range from $10^{-5}$ M to $10^{-14}$ M, preferably from $10^{-6}$ M to $10^{-10}$ M. The agriculturally appropriate solvent used in applying the composition is preferably an aqueous solvent, such as water. The composition is generally applied to the plant at any time appropriate for weed control, preferably post-emergence.

In one embodiment, the composition comprises at least one LCO with a glyphosate-based herbicide, and treatment comprises application of this composition to plants that have been genetically modified for resistance to glyphosate.

The term "plant" as used herein includes tubers, roots, stems, leaves, flowers, and fruits. The composition may be applied directly to seeds or plants or may be placed in soil in the vicinity of a seed or plant prior to or at the time of planting. In a preferred embodiment, the composition is sprayed on seeds, tubers, or foliage. Seedlings, as well as more mature plants, may be treated. Flowers and fruits may also be treated by spraying. Roots of transplants may be sprayed or dipped in the composition prior to planting.

An "effective amount" of the composition is an amount that increases plant growth or crop yield when compared with the growth or crop yield of plants or seeds that have not been treated with the composition.

The composition may be applied to monocot or dicot plants, and to legumes and non-legumes. In one embodiment, the composition is applied to field-grown plants. In another embodiment, the composition is applied to greenhouse-grown plants. For example, the composition may be applied to seeds or foliage of legumes, such as soybeans, peas, chickpeas, dry beans, peanuts, clover, alfalfa, and of non-legumes such as corn, cotton, rice, tomatoes, canola, wheat, barley, sugar beet, and grass. In general, for seed treatment, the composition is applied to seeds in a single application, and the seeds may be planted immediately or stored before planting. The composition may be applied to foliage. Foliar application generally consists of spraying the composition on the plant foliage one or more times during the growing period. In addition, if the flavonoid compound and LCO are applied sequentially, the flavonoid compound may be applied to seeds and the LCO to foliage.

EXAMPLES

1. Soybean (Northrup King S24-k4) Foliar Treatment with LCO+Chitin/Chitosan

A soybean field trial was conducted to evaluate the effects of an LCO and two commercial chitosan products on grain yield when applied to foliage alone or in combination. The two commercial chitosan products utilized in the trial were BEYOND™ (Agri-House Inc., 307 Welch Ave, Berthoud, Colo.), and ELEXA®-4PDB (Plant Defense Boosters, 235 Harrison St, Syracuse, N.Y.). The exact chitin/chitosan concentration in BEYOND™ is unknown, but is estimated to be in the range of 6-12% w/v chitosan and 0-3% w/v chitin, based on U.S. Pat. No. 6,193,988. The chitosan concentration in ELEXA®-4PDB is 4% w/v. ELEXA®-4PDB does not contain chitin. The chitosan concentration in ELEXA®-4PDB is 4% w/v. The LCO product was produced by *Rhizobium leguminosarum* by viceae and contained approximately $1 \times 10^{-8}$ M LCO. The field trial was located near Whitewater, Wis. at a site characterized by Milford silty clay loam soil. The soil had a pH of 6.6, an organic matter content of 4.8%, and phosphorus and potassium contents of 41 ppm and 131 ppm, respectively.

The soybean seed used in the study was Northrup King variety S24-K4. The LCO treatment was applied by spraying onto foliage at the V4 growth stage (see Soybean Growth and Development, *Iowa State University Extension Bulletin PM 1945*, May 2004), at a rate of 1 quart/acre in 25 gallons of water. BEYOND™ was diluted to a concentration of 0.132% w/v and ELEXA®-4PDB to 2.5% w/v in water. Each product was applied by spraying onto foliage at a rate of 1 quart/acre in 25 gallons of water. When the LCO-chitin/chitosan combination was applied, the same concentrations of LCO and chitin/chitosan products were used as when each product was applied alone.

The study was conducted in a randomized complete block design, with a plot size of 10 feet by 50 feet, 30 inch row spacing. Four replications were performed. Seeds were planted at a depth of 1 inch and a seeding rate of 175,000 seeds per acre using a John Deere 750 NT grain drill.

Results of this study are shown in Table 1. The LCO, BEYOND™, and ELEXA®-4PDB products each significantly increased grain yield by 3.5, 6.6, and 5.0 bu/acre, respectively, when applied to foliage as stand-alone treatments (p=0.1). Application of ELEXA®-4PDB in combination with LCO statistically increased yield by 6.2 bu/acre over LCO alone and 4.7 bu/acre over ELEXA®-4PDB alone. Application of BEYOND™ in combination with LCO statistically increased yield by 5.3 bu/acre over LCO alone, and numerically increased yield by 2.2 bu/acre over BEYOND™ alone.

Treatment with LCO+ELEXA®-4PDB increased yield compared to the control by 9.7 bu/acre, showing an unexpected synergistic effect of the combination compared with LCO or ELEXA®-4PDB treatment alone.

TABLE 1

| Treatment | Grain yield (bu/acre) |
| --- | --- |
| Control—non-treated | 56.2 |
| LCO | 59.7 |
| BEYOND ™ | 62.8 |
| ELEXA ®-4PDB4 PDB | 61.2 |
| LCO + BEYOND ™ | 65.0 |
| LCO + ELEXA ®-4PDB | 65.9 |
| Probability % | <0.1 |
| LSD 10% | 2.6 |
| CV % | 3.5 |

2. Soybean (Dairyland DSR 2300SR) Foliar Treatment with LCO+Chitosan

A soybean field trial was conducted to evaluate the effects of an LCO and a commercial chitosan product on grain yield when applied to foliage alone or in combination. The LCO product was the same as that used in Example 1. The commercial chitosan product utilized in the trial was ELEXA®-4PDB. The field trial was located near Whitewater, Wis. at a site characterized by Milford silty clay loam soil. The soil had a pH of 6.8, an organic matter content of 4.8%, and phosphorus and potassium contents of 46 ppm and 144 ppm, respectively.

The soybean seed used in the study was Dairyland variety DSR 2300RR. The study was conducted in a randomized complete block design, with a plot size of 10 feet by 50 feet and 15 inch row spacing. Four replications were performed. Seeds were planted at a depth of 1 inch at a seeding rate of 185,000 seeds per acre using a John Deere 750 NT grain drill.

Both LCO and ELEXA®-4PDB treatments were applied by spraying onto foliage at the V4 growth stage (see Soybean Growth and Development, *Iowa State University Extension Bulletin PM* 1945, May 2004), at a rate of 1 quart/acre in 25 gallons of water using a International Harvester Cub plot sprayer at a ground speed of 2.5 mph. When the LCO-chitosan combination was applied, the same concentrations of LCO and chitosan products were used as when each product was applied alone.

Results of this study are shown in Table 2. The LCO and ELEXA®-4PDB products numerically increased grain yield by 1.7 and 0.6 bu/acre, respectively, when applied to foliage as stand-alone treatments (p=0.1). Application of ELEXA®-4PDB in combination with LCO numerically increased yield by 0.8 bu/acre over LCO alone and 1.9 bu/acre over ELEXA®-4PDB alone. The 2.5 bu/acre increase with the combined LCO and ELEXA®-4PDB exceeded the combined benefit of the individual products alone, showing an unexpected synergistic effect of the combination.

TABLE 2

| Treatment | Grain yield (bu/acre) |
| --- | --- |
| Control—nontreated | 63.2 |
| LCO | 64.9 |
| ELEXA ®-4PDB4 PDB | 63.8 |
| LCO + ELEXA ®-4PDB | 65.7 |
| Probability % | <0.1 |
| LSD 10% | 3.9 |
| CV % | 5.3 |

3. Soybean Seed (Dairyland DSR 234RR) Treatment with LCO+Chitin/Chitosan

A soybean field trial was conducted to evaluate the effect of an LCO and two different commercial chitin/chitosan products on grain yield when applied on seed either alone or in combination. The field trial site was located near Whitewater, Wis. and characterized by Milford silty clay loam soil. Soil testing showed a soil pH of 6.8, an organic matter content of 5.1%, and phosphorus and potassium contents of 37 ppm and 136 ppm, respectively.

The LCO product used in the trial (OPTIMIZE®, EMD Crop BioScience) was produced by *Bradyrhizobium japonicum* and contained approximately $1 \times 10^{-9}$ M LCO. The two commercial chitosan products utilized in the trial were the same as those used in Example 1. The soybean seed used in the study was Dairyland variety DSR 234RR. The LCO product was sprayed onto seeds without dilution at a rate of 4.25 fl oz/cwt. BEYOND™ was diluted to 0.132% w/v and ELEXA®-4PDB to 2.5% w/v with water. Each was applied on seed at the rate of 4.25 fl oz/cwt. When the LCO-chitin/chitosan combination was applied, the same concentrations of LCO and chitin/chitosan products were used as when each product was applied alone. The combined composition was applied at 4.25 fl oz/cwt.

The study was conducted in a randomized complete block design, with a plot size of 10 feet by 50 feet, 7.5 inch row spacing. Four replications were conducted. Seeds were treated just prior to planting and were planted at a depth of 1 inch and a seeding rate of 225,000 seeds per acre using a John Deere 750 NT grain drill.

Results of the study are shown in Table 3, below. The LCO treatment numerically increased grain yield by 2.0 bu/acre relative to the non-treated control group (p=0.1). The chitosan products, BEYOND™ and ELEXA®-4PDB, each provided statistically significant increases of 2.5 and 3.4 bu/acre, respectively, over the non-treated control group. The combination of LCO and BEYOND™ significantly increased yield by 2.3 bu/acre relative to the LCO treatment alone, and numerically increased yield by 1.8 bu/acre compared to the BEYOND™ treatment alone. Treatment with a combination of LCO and ELEXA®-4PDB significantly increased yield by 2.3 bu/acre compared to the LCO treatment alone and numerically increased yield by 0.9 bu/acre relative to ELEXA®-4PDB treatment alone.

TABLE 3

| Treatment | Grain yield (bu/acre) |
| --- | --- |
| Control—non-treated | 55.5 |
| LCO | 57.5 |
| BEYOND ™ | 58.0 |
| ELEXA ®-4PDB4 PDB | 58.9 |
| LCO + BEYOND ™ | 59.8 |
| LCO + ELEXA ®-4PDB | 59.8 |
| Probability % | 9.6 |
| LSD 10% | 2.3 |
| CV % | 3.3 |

4. Corn Seed (Shur Grow SG-686-RR) Treatment with LCO+Chitin/Chitosan

A corn field trial was conducted to evaluate the effects of an LCO and commercial chitosan product on grain yield when applied on seed either alone or in combination. The field trial site was located near Marysville, Ohio and characterized by Blount silt loam soil. Soil testing showed a soil pH of 6.2 and an organic matter content of 2.7%. The field was disk cultivated in the spring prior to planting.

The LCO product used in the trial was the same as that used in Example 1. The commercial chitosan product utilized in the trial was ELEXA®-4PDB.

The corn seed used in the study was Shur Grow hybrid SG-686-RR. The seed was commercially treated with a combination of Maxim XL (0.167 fl oz/cwt, Apron XL (0.32 fl oz/cwt) and Actellic (0.03 fl oz/cwt). When used alone, the LCO product was sprayed on seed without dilution at a rate of 15 fl oz/cwt. The use rate for the chitosan product was 0.375 fl oz/cwt. The product was diluted with water and applied on seed at a slurry rate of 15 fl oz/cwt. When applied in combination, the LCO was applied at $\frac{1}{10}^{th}$ rate of 1.5 fl oz/cwt and the chitosan at a rate of 0.375 fl oz/cwt. The combined products were diluted with water and applied on seed at a slurry rate of 15 fl oz/cwt.

The study was conducted in a randomized complete block design, with four replications and a plot size of 10 feet by 20 feet, and 30 inch row spacing. Seeds were treated just prior to planting and planted at a depth of 1.5 inch and a seeding rate of 28,000 seeds per acre.

Results of the study are shown in Table 4. The LCO and chitosan treatments significantly increased yield 18.6 and 16.9 bu/acre, respectively, relative to the non-treated control group (p=0.1). In contrast, the combined LCO+chitosan treatment significantly increased yield by 40.0 bu/acre. This increase in yield was significantly greater than the individual treatments, and exceeded the combined benefit of the of the individual LCO and chitosan treatments.

TABLE 4

| Treatment | Grain yield (bu/acre) |
|---|---|
| Control—nontreated | 116.9 |
| LCO | 135.5 |
| ELEXA ®-4PDB4 PDB | 133.8 |
| LCO + ELEXA ®-4PDB | 156.9 |
| Probability % | 0.0001 |
| LSD 10% | 9.3 |
| CV % | 5.3 |

5. Corn Seed (Dairyland DSR-8194) Treatment with LCO+ Chitin/Chitosan

A corn field trial was conducted to evaluate the effects of the *Rhizobium leguminosarum* by viceae-based LCO and the two chitosan products referenced in Example 1 on grain yield when applied on corn seed alone or in combination. The field trial was conducted at a location near Whitewater, Wis., characterized by Milford silty clay loam soil. The soil had a pH of 6.5, an organic matter content of 4.5%, and phosphorus and potassium contents of 40 and 142 ppm, respectively.

Dairyland variety DSR 8194 YGPL corn seed was used in the study. The LCO product was applied without dilution on seed at a rate of 15.3 fl oz/cwt. BEYOND™ was diluted to a concentration of 0.132% w/v and ELEXA®-4PDB 2.5% w/v with water. Each was applied by spraying on seed at the rate of 15.3 fl oz/cwt. When the LCO-chitin/chitosan combination was applied, the same concentrations of LCO and chitin/chitosan products were used as when each of these products was applied alone.

The study was conducted in a randomized complete block design, with a plot size of 15 feet by 50 feet, 30 inch row spacing. Four replications were performed. Seeds were treated just prior to planting and were planted at a depth of 2" at a seeding rate of 33,000 seeds per acre. Seeds were planted with a John Deere Max Emerge II NT 6-row corn planter. Starter fertilizer (7-21-7) was applied at a rate of 200 lb/acre, with a subsequent application of 160 units nitrogen as 28% nitrogen.

The results are shown in Table 5. LCO treatment significantly increased grain yield by 4.6 bu/acre relative to the non-treated control group (p=0.1). Seeds treated with the BEYOND™ product alone showed a numerical yield increase of 3.7 bu/acre, while seed treatment with ELEXA®-4PDB alone showed no effect on grain yield. Combined treatment with LCO and BEYOND™ numerically increased grain yield by 2.1 bu/acre over LCO alone and 3.0 bu/acre over BEYOND™ alone.

Combined treatment with LCO and ELEXA®-4PDB significantly increased grain yield by 8.4 bu/acre compared with ELEXA®-4PDB treatment alone, and numerically increased grain yield by 3.7 bu/acre compared with LCO treatment alone. The LCO and ELEXA®-4PDB combination increased yield to a greater extent than the additive effects of LCO or ELEXA®-4PDB treatment alone, showing a synergistic effect of the combined treatment.

TABLE 5

| Treatment | Grain yield (bu/acre) |
|---|---|
| Control—non-treated | 162.1 |
| LCO | 166.7 |

TABLE 5-continued

| Treatment | Grain yield (bu/acre) |
|---|---|
| BEYOND ™ | 165.8 |
| ELEXA ®-4PDB4 PDB | 162.0 |
| LCO + BEYOND ™ | 168.8 |
| LCO + ELEXA ®-4PDB | 170.4 |
| Probability % | <0.1 |
| LSD 10% | 3.9 |
| CV % | 2.0 |

6. Corn (Jung 6573RR/YGPL) Foliar Treatment with LCO+ Chitin/Chitosan

A corn field trial was conducted evaluating the effect of the *Rhizobium leguminosarum* by viceae-based LCO and the two chitosan products described in Example 1 on grain yield when applied as a foliar application alone or in combination. The field trial was located near Whitewater, Wis. at a site with Milford silty clay loam soil. The soil had a pH of 6.5, and soil test results showed an organic matter content of 4.5%, and phosphorus and potassium contents of 40 and 142 ppm, respectively.

The corn seed used in the study was Jung variety 6573RR/YGPL. The LCO product was applied on the foliage at the V4 growth stage at a rate of 1 quart/acre in 25 gallons of water. BEYOND™ and ELEXA®-4PDB were diluted to concentrations of 0.132% w/v and 2.5% w/v, respectively, in water and applied on foliage at a rate of 25 gallons/acre. When the LCO-chitin/chitosan combination was applied, the same concentrations of LCO and chitin/chitosan products were used as when each of these products was applied alone.

The study was conducted in a randomized complete block design with a plot size of 15 feet by 50 feet, 30 inch row spacing. Four replications were performed. Seeds were planted at a depth of 2 inches and a seeding rate of 33,000 seeds per acre using a John Deere Max Emerge II NT 6-row corn planter. Starter fertilizer (7-21-7) was applied at a rate of 200 lb/acre, with a subsequent application of 160 units nitrogen as 28% nitrogen.

Results of this study are shown in Table 6. The LCO, BEYOND™, and ELEXA®-4PDB products significantly increased grain yield over the non-treated control group by 11.3, 8.8, and 7.4 bu/acre, respectively, when applied to foliage as stand-alone treatments (p=0.1). Application of ELEXA®-4PDB in combination with LCO further increased yield by 1.1 bu/acre compared with ELEXA®-4PDB alone, and 5.0 bu/acre compared with LCO alone. Application of BEYOND™ in combination with LCO further increased yield by 2.3 bu/acre compared with LCO alone, and 4.8 bu/acre compared with BEYOND™ alone.

TABLE 6

| Treatment | Grain yield (bu/acre) |
|---|---|
| Control—non-treated | 162.6 |
| LCO | 173.9 |
| BEYOND ™ | 171.4 |
| ELEXA ®-4PDB4 PDB | 170.0 |
| LCO + BEYOND ™ | 176.2 |
| LCO + ELEXA ®-4PDB | 175.0 |
| Probability % | 0.3 |
| LSD 10% | 6.5 |
| CV % | 3.2 |

7. Corn Seed (Pioneer 38H52) Treatment with LCO+Flavonoid

A corn field trial was conducted evaluating the effect of liquid formulations of LCO and flavonoid on grain yield when applied alone or in combination on seed. The field trial was conducted at a site near Whitewater, Wis. in a Plano silt loam soil. The soil had a pH of 6.5 and soil test results showed an organic matter content of 4.4% and phosphorus and potassium content of 42 and 146 ppm, respectively. The field was previously planted to soybeans. It was fall chisel plowed and field cultivated in the spring prior to planting.

The LCO product used in the trial was the same as that used in Example 1. The flavonoid product used (ReVV®, EMD Crop BioScience) had a 10 mM total flavonoid concentration comprising genistein and daidzein.

The corn seed used in the trial was Pioneer variety 38H52. The use rate for the LCO and flavonoid products were 1.5 and 0.184 fl oz/cwt, respectively. The products were each diluted with water and applied on seed at a slurry rate of 15.3 fl oz/cwt. The LCO/flavonoid combination was applied at the same concentration and slurry rate as when applied alone. The study was conducted in a randomized complete block design, with a plot size of 10 feet by 50 feet, with 30 inch row spacing, and four replications per treatment. Seeds were planted at a depth of 2 inches at a seeding rate of 33,000 seeds per acre. Planting was carried out using a four row precision vacuum planter. One hundred and forty units of nitrogen were applied as urea in advance of planting, and an additional 150 lb of 7-21-7 starter fertilizer was applied at planting.

Results of the study are shown in Table 7. The flavonoid treatment statistically increased grain yield by 5.3 bu/acre, while the LCO treatment numerically increased grain yield by 3.3 bu/acre. Application of the two products in combination resulted in a statistically significant increase in yield over each of the two products administered alone. The increase observed with the combination treatment of 19.2 bu/acre unexpectedly exceeded the combined effect of the individual products alone (8.6 bu/acre) by more than two-fold, demonstrating a synergistic effect of the combination treatment.

TABLE 7

| Treatment | Application | Grain yield (bu/acre) |
|---|---|---|
| Control | None | 142.5 |
| LCO | Seed | 145.8 |
| Flavonoid | Seed | 147.8 |
| Flavonoid + LCO | Seed | 161.7 |
| Probability % | | <0.1 |
| LSD 10% | | 4.2 |
| CV % | | 4.4 |

8. Corn Seed (DynaGro 51K74) Treatment with LCO+Flavonoid

A second corn trial was conducted as described in Example 7 at a location near Fergus Falls, Minn., in a nutrient rich loam soil previously planted to soybeans. The LCO and flavonoid products were applied alone or in combination on DynaGro variety 51K74 corn seed. The study was conducted in a randomized complete block design, with a plot size of 10 feet by 20 feet, with 30 inch row spacing, and four replications per treatment.

Results of the study are shown in Table 8. The LCO and flavonoid seed treatments numerically increased grain yield compared to the non-treated control by 7.3 and 15.3 bu/acre, respectively. Application of the two products in combination statistically increased yield compared to the control by 24.0 bu/acre, and by 17.1 bu/acre compared to the LCO treatment. The increase in yield observed with the combined treatment exceeded the combined increase in yield from the individual products alone.

TABLE 8

| Treatment | Application | Grain yield (bu/acre) |
|---|---|---|
| Control | None | 141.2 |
| LCO | Seed | 148.5 |
| Flavonoid | Seed | 156.5 |
| Flavonoid + LCO | Seed | 165.2 |
| Probability % | | <0.1 |
| LSD 5% | | 13.9 |
| CV % | | 6.3 |

9. Corn (Dairyland DSR 4497) Seed, Furrow, and Foliage Treatment with LCO+Flavonoid A corn field trial was conducted at the same site described above in Example 7 to evaluate the effect of flavonoid seed treatment on grain yield compared to application of LCO either in the seed furrow at planting or spray-applied as a foliar application. These individual product treatments were additionally compared to flavonoid seed treatment combined with in-furrow LCO application and flavonoid seed treatment combined with foliar LCO application. The LCO and flavonoid products were is the same as those used in the prior examples.

The corn seed used in the trial was Dairyland variety DSR 4497. The flavonoid product was applied on seed at the same use rate of 0.184 fl oz/cwt and slurry rate in water of 15.3 fl oz/cwt as in prior examples. The LCO product was applied at planting in the seed furrow at a rate of 1 pint/acre in 5 gallons of water, or spray-applied to foliar surfaces at a rate of 1 qt/acre in 25 gallons of water at the V4 stage of corn development. The seed/furrow and seed/foliar applications were at the same rates for the combination as when applied alone.

The study was conducted in a randomized complete block design, with a plot size of 10 feet by 50 feet, with 30 inch row spacing, and four replications per treatment. Seeds were planted at a depth of 2 inches at a seeding rate of 33,000 seeds per acre. Planting was carried out using a four row precision vacuum planter. One hundred and forty units of nitrogen were applied as urea in advance of planting, and an additional 150 lb of 7-21-7 starter fertilizer was applied at planting.

Results of the study are shown in Table 9. Application of flavonoid on seed and LCO in the seed furrow numerically increased grain yield by 4.3 and 2.6 bu/acre, respectively, compared to the control treatment. In contrast, combined application of the two products on seed and in furrow statistically increased yield by 5.5 bu/acre.

Separate application of flavonoid on seed and LCO as a foliar application resulted in a numerical increase in yield with flavonoid seed treatment of 4.3 bu/acre and a statistically significant increase of 7.4 bu/acre with LCO foliar application. Combined flavonoid seed treatment and LCO foliar application further increased yield by 9.2 bu/acre compared to the control treatment.

TABLE 9

| Treatment | Application | Grain yield (bu/acre) |
|---|---|---|
| Control | None | 173.6 |
| Flavonoid | Seed | 177.9 |
| LCO | Furrow | 176.0 |
| LCO | Foliar | 181.0 |
| Flavonoid/LCO | Seed, furrow | 179.1 |
| Flavonoid/LCO | Seed, foliar | 182.8 |
| Probability % | | <0.1 |
| LSD 10% | | 4.9 |
| CV % | | 5.3 |

10. Corn (Spangler 5775) Seed, Furrow, and Foliage Treatment with LCO+Flavonoid A parallel corn field trial was conducted at the same location and with the same treatments and trial design as described in Example 9, but differing in the variety of corn used (Spangler 5775).

Results of the study are shown in Table 10. Application of flavonoid on seed statistically increased grain yield by 7.4 bu/acre compared to the non-treated control, while LCO application in the seed furrow numerically increased grain yield by 3.5 bu/acre. Combined flavonoid seed treatment and LCO furrow application further increased yield by 9.7 bu/acre compared to the control treatment.

Separate application of flavonoid on seed and LCO as a foliar application resulted in a statistically significant increase in yield with flavonoid seed treatment of 7.4 bu/acre (as stated above) and a numerical increase of 1.1 bu/acre with LCO foliar application. Application of the two products in combination resulted in a statistically significant increase in yield greater than that seen for each of the two products alone. Further, the increase observed with the combination treatment (16.2 bu/acre) exceeded the combined effect of the individual products alone (8.5 bu/acre), showing a synergistic effect of the combination treatments.

TABLE 10

| Treatment | Application | Grain yield (bu/acre) |
|---|---|---|
| Control | None | 160.7 |
| Flavonoid | Seed | 168.1 |
| LCO | Furrow | 164.2 |
| LCO | Foliar | 161.8 |
| Flavonoid/LCO | Seed, furrow | 170.4 |
| Flavonoid/LCO | Seed, foliar | 176.9 |
| Probability % | | <0.1 |
| LSD 10% | | 5.6 |
| CV % | | 4.8 |

11. LCO Foliar and Flavonoid Seed Treatment of Soybean (Dairyland DSR 1701)

A soybean field trial was conducted to evaluate the effect of flavonoid seed treatment on grain yield compared to the effect of foliar application of LCO. The individual product treatments were additionally compared to flavonoid seed treatment combined with LCO foliar application. The LCO product, was the same as that used in Example 1, and the flavonoid product was the same as that used in prior examples.

The field trial was conducted at a site near Whitewater, Wis. in a Milford silty clay loam soil. The soil had a pH of 6.5 and soil test results showed an organic matter content of 4.7% and phosphorus and potassium content of 48 and 136 ppm, respectively. The field was no-till and was previously planted to corn.

The soybean seed used in the trial was Dairyland variety DSR 1701. The flavonoid product was applied at a use rate of 0.184 fl oz/cwt and slurry rate in water of 4.25 fl oz/cwt. The LCO product was spray-applied to foliar surfaces at a rate of 1 qt/acre in 25 gallons of water at the V4 stage of soybean development. The combined seed/foliar application was at the same rate as when applied alone. The study was conducted in a randomized complete block design, with a plot size of 10 feet by 50 feet, with 30 inch row spacing, and four replications per treatment. Seeds were planted at a depth of 1 inch at a seeding rate of 160,000 seeds per acre. Planting was carried out using a John Deere 750 NT grain drill.

Results of the study are shown in Table 11. Application of flavonoid on seed statistically increased grain yield by 3.2 bu/acre compared to the non-treated control, while LCO foliar application numerically increased grain yield by 1.2 bu/acre. Application of the two products in combination resulted in a statistically significant increase above each of the two products alone, with the increase in yield (5.0 bu/acre) exceeding the combined effect of the individual products alone (4.4 bu/acre), showing a synergistic effect of the combination treatment.

TABLE 11

| Treatment | Application | Grain yield (bu/acre) |
|---|---|---|
| Control | None | 47.8 |
| Flavonoid | Seed | 51.0 |
| LCO | Foliar | 49.0 |
| Flavonoid/LCO | Seed/foliar | 52.8 |
| Probability % | | <0.1 |
| LSD 10% | | 1.3 |
| CV % | | 5.2 |

12. LCO Foliar and Flavonoid Seed Treatment of Soybean (Dairyland DSR 2000)

A parallel soybean field trial was conducted at the same location and with the same treatments and trial design as described in Example 11, but differing in the variety of soybean used (Dairyland variety DSR 2000).

Results of the study are shown in Table 12. Application of flavonoid on seed and LCO as a foliar application statistically increased grain yield by 2.6 and 4.5 bu/acre, respectively, compared to the non-treated control. Combined flavonoid seed treatment and LCO foliar application further increased yield by 7.1 bu/acre compared to the control treatment.

TABLE 12

| Treatment | Application | Grain yield (bu/acre) |
|---|---|---|
| Control | None | 40.9 |
| Flavonoid | Seed | 43.5 |
| LCO | Foliar | 45.4 |
| Flavonoid/LCO | Seed/foliar | 48.0 |
| Probability % | | <0.1 |
| LSD 10% | | 1.8 |
| CV % | | 4.5 |

13. Soybean Seed (Dairyland DSR 2300RR) Treatment with LCO+Flavonoid

A soybean field trial was conducted to evaluate the effect of LCO and flavonoid products on grain yield when applied on seed either alone or in combination. The field trial site was located near Whitewater, Wis. and characterized by Plano silt loam soil. Soil testing showed a soil pH of 6.5, an organic matter content of 3.9%, and phosphorus and potassium contents of 40 ppm and 138 ppm, respectively. The field was no-till and was previously planted to corn.

The LCO product used in the trial (OPTIMIZE®, EMD Crop BioScience) was produced by *Bradyrhizobium japonicum* and contained approximately $1 \times 10^{-9}$ M LCO. The flavonoid product used (ReVV®, EMD Crop BioScience) had a 10 mM total flavonoid concentration comprising genistein and daidzein in a ratio of 8:2 w/w.

The soybean seed used in the study was Dairyland variety DSR 2300RR. The LCO and flavonoid products were sprayed onto seeds alone or in combination at a rate of 4.25 and 0.184 fl oz/cwt, respectively. The study was conducted in a randomized complete block design, with four replications and a plot size of 10 feet by 50 feet, and 15 inch row spacing. Seeds were treated just prior to planting and planted at a depth of 1 inch and a seeding rate of 185,000 seeds per acre using a John Deere 750 NT grain drill.

Results of the study are shown in Table 13. The LCO and flavonoid treatments numerically increased yield 2.9 and 4.0 bu/acre, respectively, relative to the non-treated control group (p=0.1). In contrast, the combined LCO+flavonoid treatment significantly increased yield by 7.0 bu/acre. This increase in yield was greater than the combined benefit of the of the individual LCO and flavonoid treatments.

TABLE 13

| Treatment | Grain yield (bu/acre) |
| --- | --- |
| Control—nontreated | 54.1 |
| LCO | 57.0 |
| Flavonoid | 58.1 |
| LCO + flavonoid | 61.1 |
| Probability % | <0.1 |
| LSD 10% | 4.2 |
| CV % | 3.6 |

14. Corn (Pioneer Hybrid 34A17) Foliar Treatment with LCO+Flavonoid or LCO+Chitosan A corn field trial was conducted to evaluate the effects of LCO/flavonoid, and LCO/chitosan products on grain yield when applied to foliage alone or in combination. The LCO product was produced by *Rhizobium leguminosarum* by viceae and contained approximately $10^{-8}$ M LCO. The flavonoid product used had a 10 mM total flavonoid concentration comprising genistein and daidzein in a ratio of 8:2 w/w. The chitosan product (ELEXA®-4PDB) was the same as that used in the prior examples.

The field trial was located near York, Nebr. at a site characterized by Hastings silt loam soil. The soil had a pH of 6 and an organic matter content of 3%. The site was conventionally tilled, and the prior crop was soybeans. The corn seed used in the study was Pioneer hybrid 34A17. The study was conducted in a randomized complete block design, with a plot size of 10 feet by 30 feet and 30 inch row spacing. Four replications were performed. Seeds were planted at a depth of 2 inches at a seeding rate of 30,200 seeds per acre.

Treatments were applied by spraying onto foliage at the V5 growth stage. The LCO and ELEXA®-4PDB treatments were applied at a rate of 1 quart/acre in 20 gallons of water using a small plot sprayer at a ground speed of 2.3 mph. The flavonoid treatment was initially diluted 25× in water, then applied at a rate of 1 quart/acre in 20 gallons of water. The LCO-chitosan combination treatment was applied at a reduced rate of 3.2 fl oz/acre of LCO and 12.8 fl oz chitosan in 20 gallons of water. For the LCO-flavonoid combination, the flavonoid was first diluted 25× in water, then applied similarly to the LCO-chitosan combination at 3.2+12.8 fl oz/acre diluted in 20 gallons of water.

Results of this study are shown in Table 14. The LCO, flavonoid, and ELEXA®-4PDB treatments numerically increased grain yield by 1.2, 3.5, and 1.5 bu/acre, respectively, when applied to foliage as stand-alone treatments (p=0.1). Combined is application of LCO with flavonoid and LCO with ELEXA®-4PDB significantly increased yield by 8.6 and 12.1 bu/acre compared to the control treatment. In each case, the combined treatment response exceeded the combined benefit of the individual products alone, demonstrating a synergistic effect of the combination compositions. This occurred even though the combination products were applied at reduced rates compared to when applied alone.

TABLE 14

| Treatment | Grain yield (bu/acre) |
| --- | --- |
| Control—nontreated | 222.0 |
| LCO | 223.2 |
| Flavonoid | 225.5 |
| ELEXA ®-4PDB4 PDB | 223.5 |
| LCO + flavonoid | 230.6 |
| LCO + ELEXA ®-4PDB | 234.1 |
| Probability % | 0.0909 |
| LSD 10% | 6.5 |
| CV % | 2.4 |

15. Corn (Midwest Seed Genetics Hybrid 8463859 RR2) Foliar Treatment with LCO+Flavonoid or LCO+Chitosan A corn field trial was conducted similar to that of Example 14 to evaluate the effects of LCO/flavonoid, and LCO/chitosan products on grain yield when applied to foliage alone or in combination. The LCO, flavonoid, and chitosan products were the same as that used in Example 14.

The field trial was located near Sparta, Ill. at a site characterized by silt loam soil. The soil had a pH of 6.5 and an organic matter content of 2.6%. The site was conventionally tilled, and the prior crop was soybeans. The corn seed used in the study was Midwest Seed Genetics hybrid 8463859 RR2. The study was conducted in a randomized complete block design, with a plot size of 10 feet by 40 feet and 30 inch row spacing. Four replications were performed. Seeds were planted at a depth of 2 inches at a seeding rate of 26,100 seeds per acre.

Treatments were applied by spraying onto foliage at the V3-V4 growth stage. The individual and combined treatments were applied at the rates described in Example 14 in 20 gallons of water using a backpack sprayer at a ground speed of 3 mph.

Results of this study are shown in Table 15. The LCO, flavonoid, and ELEXA®-4PDB treatments numerically increased grain yield by 3.4, 7.1, and 3.3 bu/acre, respectively, when applied to foliage as stand-alone treatments (p=0.1). Combined application of LCO with flavonoid significantly increased yield by 16.5, while combined application of LCO with ELEXA®-4PDB numerically increased yield by 10.5 bu/acre compared to the control treatment. In each case, the combined treatment response exceeded the combined benefit of the individual products alone, demonstrating a synergistic effect of the combination compositions. This occurred even though the combination products were applied at reduced rate compared to when applied alone.

TABLE 15

| Treatment | Grain yield (bu/acre) |
| --- | --- |
| Control—nontreated | 71.7 |
| LCO | 75.1 |
| Flavonoid | 78.8 |
| ELEXA ®-4PDB4 PDB | 75.0 |
| LCO + flavonoid | 88.2 |
| LCO + ELEXA ®-4PDB | 82.2 |
| Probability % | 0.6459 |
| LSD 10% | 13.8 |
| CV % | 14.6 |

16. Corn Foliar Treatment with LCO and Herbicide

Three corn field trials were conducted to evaluate the effect of foliar application of LCO in combination with four different herbicides. The LCO is the same as that used in prior foliar application examples. The herbicides included glyphosate (Roundup Original Max®, Monsanto Company, St. Louis, Mo.), glufosinate-ammonium (Liberty®, Bayer CropScience LP, Research Triangle Park, N.C.), mesotrione (Calisto®, Syngenta Crop Protection, Inc., Greensboro, N.C.), and nicosulfu/rimsulfuron (Steadfast®, E. I. du Pont de Nemours and Company, Wilmington, Del.).

Two of the trials were located near Whitewater, Wis. at sites characterized by Milford silty clay loam soil (fields F-5 and P-1). The F-5 site was conventionally tilled with a prior crop of corn, and the P-1 site was minimum tilled with soybean as the prior crop. The corn seed used for both studies was Pioneer hybrid 36B05 HXX/RR/LL. The studies were conducted in a randomized complete block design, with a plot size of 10 feet by 50 feet, 30 inch row spacing, and four replications. Seeds were planted at a depth of 2 inches at a seeding rate of 33,000 seeds per acre using a vacuum precision plot planter.

The third field trial was located near York, Nebr. at a site characterized by Hastings silt loam soil. The site was conventionally tilled with h soybean as the prior crop. The corn seed used in the study was Pioneer hybrid 34A17. The study was conducted in a randomized complete block design, with a plot size of 10 feet by 30 feet, 30 inch row spacing, and four replications. Seeds were planted at a depth of 2 inches at a seeding rate of 30,200 seeds per acre.

Treatments at the two Whitewater, Wis. sites were applied by spraying onto foliage at the V4 growth stage. The LCO treatment was applied at a rate of 1 quart/acre; the herbicide products were applied at label rate for each product. The herbicide and LCO+herbicide treatments were foliar-applied in 25 gallons of water using a small plot sprayer at a ground speed of 2.5 mph. Treatments at the York, Nebr. site were applied at the V6 growth stage at the same 1 quart/acre for the LCO and label rate for the herbicide products in 20 gallons of water using a small plot sprayer at a ground speed of 2.3 mph.

Results of this study are shown in Table 16. With the two Whitewater, Wis. trials, application of LCO in combination with the four different herbicides enhanced grain yield compared to the herbicide alone with all LCO/herbicide combinations at the two locations, with the exception of the LCO+Steadfast combination at the P-1 site. At the York, Nebr. location, application of LCO in combination with the four different herbicides enhanced grain yield compared to the herbicide alone with each of the LCO/herbicide combinations, with the exception of the LCO+Calisto treatment.

TABLE 16

| Trial location | Round-Up | LCO + Round-Up 1 qt/A | Liberty | LCO + Liberty 1 qt/A | Calisto | LCO + Calisto 1 qt/A | Steadfast | LCO + Steadfast 1 qt/A |
|---|---|---|---|---|---|---|---|---|
| Whitewater. WI | 157.5 | 161.9 | 152.1 | 156.9 | 156 | 158.8 | 140.6 | 141.2 |
| Whitewater. WI | 161.2 | 169.2 | 159.6 | 164.2 | 162.8 | 169.1 | 154.4 | 152.1 |
| York, NE | 195.8 | 204.6 | 201 | 208.9 | 202.8 | 202 | 194.3 | 201.3 |

Although preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A method for enhancing plant growth and/or crop yield, comprising:
    applying an effective amount of a first composition to a seed and/or to the plant that grows from said seed, said first composition comprising at least one lipo-chitooligosaccharide,
    applying an effective amount of a second composition to said seed and/or to the plant that grows from said seed, said second composition comprising at least one chitin or at least one chitosan,
    wherein application of the first composition and second composition, in combination, enhances crop yield by at least about 2 bushels per acre as compared to that of a seed and/or plant to which only one of the first composition and second composition is applied.

2. The method of claim 1, further comprising applying at least one herbicide to said seed and/or to the plant that grows from said seed.

3. The method of claim 2, wherein the at least one herbicide comprises bentazon, acifluorfen, chiorimuron, lactofen, clomazone, fluazifop, glufosinate, glyphosate, sethoxydim, imazethapyr, imazamox, fomesafe, flumiclorac, imazaquin, and/or clethodim.

4. The method of claim 2, wherein said seed is genetically modified for resistance to one or more herbicides.

5. The method of claim 1, wherein the second composition comprises at least one chitin.

6. The method of claim 1, wherein the second composition comprises at least one chitosan.

7. The method of claim 1, wherein said seed is a legume seed.

8. The method of claim 1, wherein said seed is a non-legume seed.

9. The method of claim 1, wherein said is selected from the group consisting of soybeans, peas, chickpeas, drybeans, peanuts, clover, alfalfa, corn, cotton, rice, tomatoes, canola, wheat, barley, sugar beet, and grass.

10. The method of claim 1, wherein said first composition has a lipo-chitooligosaccharide concentration between $10^{-14}$ and $10^{-5}$ M.

11. The method of claim 1, wherein said first composition has a lipo-chitooligosaccharide concentration between $10^{-10}$ and $10^{-6}$ M.

12. The method of claim 1, wherein said second composition has a chitinous compound concentration between 0.1 and 15% w/v.

13. The method of claim 1, wherein said second composition has a chitinous compound concentration between 3 and 12% w/v.

14. The method of claim 1, wherein the first and second compositions are applied to the seed prior to planting.

15. The method of claim 1, wherein the first and second compositions are applied sequentially.

16. The method of claim 1, wherein the first and second compositions are applied concurrently.

17. The method of claim 1, wherein crop yield is enhanced by at least about 3 bushels per acre as compared to that of a seed and/or plant to which only one of the first composition and second composition is applied.

18. The method of claim 1, wherein crop yield is enhanced by at least about 4 bushels per acre as compared to that of a seed and/or plant to which only one of the first composition and second composition is applied.

19. The method of claim 1, wherein crop yield is enhanced by at least about 5 bushels per acre as compared to that of a seed and/or plant to which only one of the first composition and second composition is applied.

20. The method of claim 1, wherein crop yield is enhanced by at least about 6 bushels per acre as compared to that of a seed and/or plant to which only one of the first composition and second composition is applied.

\* \* \* \* \*